United States Patent [19]
Asakawa et al.

[11] Patent Number: 6,063,302
[45] Date of Patent: *May 16, 2000

[54] METHOD FOR HANDLING IMINOCARBOXYLIC ACID SALT

[75] Inventors: Miaki Asakawa; Yasutaka Sumida; Yuichi Kita, all of Hyogo, Japan

[73] Assignee: Nippon Shokubai Co., Ltd., Osaka-fu, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/544,784

[22] Filed: Oct. 18, 1995

[30] Foreign Application Priority Data

Oct. 20, 1994 [JP] Japan .................................. 6-254935
Oct. 20, 1994 [JP] Japan .................................. 6-254936
Sep. 28, 1995 [JP] Japan .................................. 7-250531

[51] Int. Cl.$^7$ .......................... C09K 31/02; C07C 229/00
[52] U.S. Cl. ................................. 252/1; 562/571; 562/568
[58] Field of Search ................... 562/571, 568; 252/1

[56] References Cited

U.S. PATENT DOCUMENTS 5,318,726   6/1994   Rossmaier et al. .

FOREIGN PATENT DOCUMENTS 05170714   7/1993   Japan .

OTHER PUBLICATIONS

European Search Report EP 95 30 7462, Jan. 19, 1996.
Derwent publication of JP 6–41030 (1994).
Patent Abstract of Japan, of JP 5170714 (1993).
Derwent publication, JP 5–58929 (1993).

*Primary Examiner*—D. Gabrielle Brouillette
*Assistant Examiner*—Monique Cole
*Attorney, Agent, or Firm*—Omri M. Behr, Esq.

[57] ABSTRACT

An aqueous iminocarboxylic acid salt solution composition the iminocarboxylic acid salt of which has a structure of the formula (II):

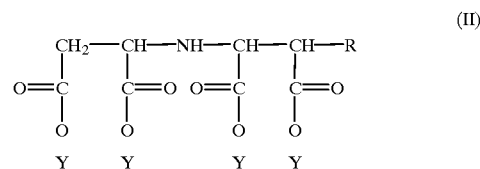

wherein R is a hydrogen atom or a hydroxyl group and Y is a sodium atom, a potassium atom, or an ammonium group, contains an aspartic acid backbone moiety whose molar ratio of the isomers, i.e. D form/L form, is in the range of 1/0 to 0.7/0.3 or D form/L form, in the range of 0/1 to 0.3/0.7, and accounts for a concentration in the range of 40 to 70% by weight and a method for handling the composition while keeping the pH value thereof kept in the range of 7 to 12.

8 Claims, No Drawings

METHOD FOR HANDLING IMINOCARBOXYLIC ACID SALT

BACKGROUND OF THE INVENTION

1. Field of the Invention

This invention relates to an aqueous iminocarboxylic acid salt solution composition and a method for the handling of an iminocarboxylic acid salt. More particularly, it relates to the aqueous solution composition of an iminocarboxylic acid salt useful as an organic chelating agent, a detergent builder, a descaling agent, etc. and a method for handling the iminocarboxylic acid salt in the form of a stable and homogeneous aqueous solution without entraining precipitation of iminocarboxylic acid salt crystals for a long time.

The term "handling" as used in this invention refers to the transportation of the aqueous solution of an iminocarboxylic acid salt as by means of a tank lorry, the storage thereof as in a tank, the conveyance thereof as by a piping inclusive of pipes, valves, and nozzles, and the like.

2. Description of the Prior Art

The iminocarboxylic acid salts which are represented by such formula (I) and formula (II) as will be described specifically afterward have been known because of their disclosure in JP-A-05-170,714. When such an iminocarboxylic acid salt as mentioned above is handled in a solid state such as of a powder or granules, since this salt has high hygroscopicity, the individual solid particles thereof in the course of handling absorb the moisture suspended in the ambient air and ultimately form viscous lumps by virtue of fusion.

It is, accordingly, proper to handle the iminocarboxylic acid salt in the form of an aqueous solution. No concrete study has ever been made as to the handling of the salt in the form of an aqueous solution. For the first time in the art, our study has confirmed that various problems are encountered in the handling of the iminocarboxylic acid salt in the form of an aqueous solution. One of the problems resides in the precipitation of the salt in the aqueous solution. Generally, it is economical to handle this aqueous solution at its highest allowable concentration at a low temperature. Under the conditions of such high concentration and such low temperature, however, the aqueous solution precipitates iminocarboxylic acid salt crystals and particularly the elapse of time proportionately aggravates this precipitation. In an extreme case, the precipitation may end up in solidification of the whole of the aqueous solution itself. Especially, for the sodium salt of an iminocarboxylic acid, the problem of this precipitation is serious because this salt is deficient in solubility in water as compared with other salts of the acid. Another problem consists in the viscosity of the aqueous iminocarboxylic acid salt solution. If the aqueous solution avoids precipitating such crystals and nevertheless exhibits such high viscosity as exceeds 10,000 cps, the difficulty with which it is handled will be exaggerated notably. Yet another problem resides in the fact that an attempt to heighten the concentration of the aqueous solution of an iminocarboxylic acid salt to a desired level by heating this solution results in coloring the iminocarboxylic acid salt or the aqueous solution thereof possibly to the extent of seriously impairing the commercial value thereof and moreover inducing the precipitation of the iminocarboxylic acid salt in the aqueous solution.

An object of this invention, therefore, is to provide a novel aqueous solution composition of an iminocarboxylic acid salt and a method for handling the composition.

Another object of this invention is to provide the aqueous solution composition of an iminocarboxylic acid salt so stable that the composition, when used as a chelating agent, for example, permits easy handling in the form of a homogeneous solution and avoids precipitating crystals even at low temperatures.

Yet another object of this invention is to solve the afore-mentioned problems which are encountered when an iminocarboxylic acid salt is handled in the form of an aqueous solution and provide a method for enabling the aqueous iminocarboxylic acid salt solution to be stably handled for a long time.

SUMMARY OF THE INVENTION

The objects mentioned above are accomplished by an aqueous iminocarboxylic acid salt solution composition characterized in that the iminocarboxylic acid salt thereof has a structure of the formula (I):

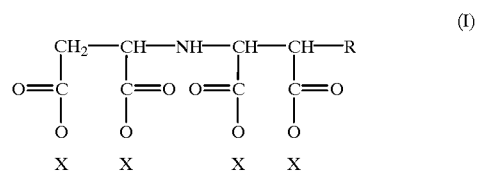

wherein R is a hydrogen atom or a hydroxyl group and X is a sodium atom or an ammonium group, contains an aspartic acid backbone moiety whose molar ratio of the isomers, i.e. D form/L form, is in the range of 1/0 to 0.7/0.3 or D form/L form, in the range of 0/1 to 0.3/0.7, and accounts for a concentration in the range of 40 to 70% by weight.

The objects mentioned above are further accomplished by a method for handling an iminocarboxylic acid salt represented by the formula (II):

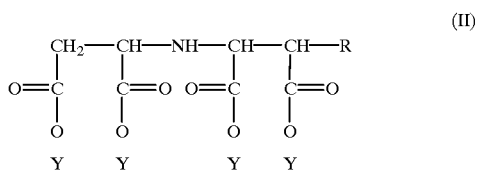

wherein R is a hydrogen atom or a hydroxyl group and Y is a sodium atom, a potassium atom, or an ammonium group characterized in that the iminocarboxylic acid salt is handled in the form of an aqueous solution wherein the iminocarboxylic acid salt contains an aspartic acid backbone moiety whose molar ratio of the isomers, i.e. D form/L form, is in the range of 1/0 to 0.7/0.3 or in the range of 0/1 to 0.3/0.7, and accounts for a concentration in the range of 40 to 70% by weight and the aqueous solution has the pH value thereof adjusted in the range of 7 to 12.

After continuing a diligent study on the matter at hand, we have learnt that an iminocarboxylic acid salt can be handled as a stable and homogeneous aqueous solution inducing neither precipitation of crystals nor solidification of aqueous solution over a long period of time by setting the molar ratio of the isomers, D form and L form, of the aspartic acid backbone moiety of the iminocarboxylate, the concentration of the iminocarboxylic acid salt in the aqueous solution, and the pH value of the aqueous solution within the respective specific ranges. We have perfected the present invention based on this knowledge.

The aqueous iminocarboxylic acid salt solution composition of this invention is a stable composition such that it can be easily stored and transported and avoid precipitating crystals even at low temperatures. Further, since the aqueous iminocarboxylic acid salt solution composition of this invention can be handled in the form of a homogeneous solution, it is useful as various species of chelating agents.

By the method of this invention, an iminocarboxylic acid salt can be stably handled in the form of an aqueous solution incapable of inducing either precipitation of iminocarboxylic acid salt crystals or solidification of the aqueous solution over a long period of time.

According to the method of this invention, the aqueous iminocarboxylic acid salt solution can be easily handled because the viscosity of this aqueous solution is not more than 10,000 cps. Since the method of this invention enables a given iminocarboxylic acid salt to be handled in the form of a stable and homogeneous aqueous solution over a long period of time without requiring any device for either heat retention or agitation, the handling is accomplished conveniently and readily.

DESCRIPTION OF THE PREFERRED EMBODIMENT

The iminocarboxylates which are represented by the formulas (I) and (II) mentioned above can be prepared by a well-known method. The compounds of the formulas (I) and (II) which have a hydroxyl group for either of Ris obtained by causing an aspartate to react with an epoxysuccinate under an alkaline condition in a water medium. The compounds of the formulas (I) and (II) which have a hydrogen atom for either of Ris obtained by causing an aspartate to react with a maleate under an alkaline condition in a water medium.

In the formulas (I) and (II), all the four X's or Y's need not be identical but may be severally different. The iminocarboxylic acid salts represented by the formulas (I) and (II) embrace disodium dipotassium salts and monosodium tripotassium salts in addition to tetrasodium salts. Particularly for the tetrasodium salts, among other salts mentioned above, the method for handling according to this invention is used effectively.

This invention resides in a low-temperature stable aqueous iminocarboxylic acid salt solution composition the iminocarboxylate of which contains an aspartic acid backbone moiety whose molar ratio of the isomers (D form/L form) is in the range of 1/0 to 0.7/0.3 or 0/1 to 0.3/0.7.

The demarcation of the molar ratio of the D form and the L form in the aspartic acid backbone of the iminocarboxylic acid salt mentioned above within the range mentioned above may be attained by either limiting the molar ratio of a D-aspartic acid and an L-aspartic acid contained in the charged raw material prior to the production of the iminocarboxylic acid salt within the aforementioned range or by mixing iminocarboxylic acid salt produced independently from a D-aspartic acid and an L-aspartic acid at a ratio equivalent to the molar ratio mentioned above.

The aqueous iminocarboxylic acid salt solution of a composition such that the molar ratio of the isomers, the D form and the L form, in the aspartic acid backbone moiety of the salt falls outside the range mentioned above suffers quick precipitation of crystals and assumes a heterogeneous slurry state at low temperatures even when the salt concentration is 30% by weight. To be handled as a homogeneous slurry, this heterogeneous slurry not only requires such special mixture as by forced circulation with a stirrer or a pump but also entrains such trouble as clogging of the pump during the course of conveyance.

The concentration of the iminocarboxylic acid salt in the aqueous solution of this invention properly is in the range of 40 to 70% by weight, preferably 40 to 60% by weight. The aqueous solution satisfying this concentration is prepared by a well-known method. If the concentration of the iminocarboxylic acid salt is higher than the upper limit of the range mentioned above, the composition will assume a slurry state of high viscosity such as to render the handling thereof difficult. Conversely, if the concentration of the iminocarboxylic acid salt is lower than the lower limit of the range, the aqueous solution, though permitting easy handling, will require the container used for the storage or transportation thereof to be so enlarged as to render the work of storage or transportation uneconomical.

The aqueous iminocarboxylic acid salt solution composition prepared as described above can be handled as a stable and homogeneous solution for a long time without suffering precipitation of crystals even at such low temperatures as fall in the range of from 20° to –10° C.

The first essential requirement for the method of handling according to this invention is that the molar ratio of the D form and the L form (D form/L form) in the aspartic acid backbone of the iminocarboxylic acid salt be set in the range of 1/0 to 0.7/0.3 (D form+L form=1 mol) or 0/1 to 0.3/0.7 (D form+L form=1 mol). The demarcation of the molar ratio of the D form and the L form in the aspartic acid backbone of the iminocarboxylic acid salt mentioned above within the range mentioned above may be attained by either limiting the molar ratio of a D-aspartic acid and an L-aspartic acid contained in the charged raw material prior to the production of the iminocarboxylic acid salt within the range or by mixing iminocarboxylic acid salts produced independently from a D-aspartic acid and an L-aspartic acid at a ratio equivalent to the molar ratio mentioned above. An iminocarboxylic acid salt of a composition such that the ratio of the D form and the L form in the aspartic acid backbone thereof falls outside the range mentioned above, when handled in the form of an aqueous solution, quickly precipitates crystals and assumes a heterogeneous slurry state even when the other essential requirements for the handling are satisfied. To be handled as a homogeneous slurry, this heterogeneous slurry not only requires such special mixture as by forced circulation with a stirrer or a pump but also entrains such trouble as clogging of the pump during the course of conveyance.

The second essential requirement for the method of handling according to this invention resides in limiting the concentration of the aqueous iminocarboxylic acid salt solution to the range of 40 to 70% by weight. If the concentration of this aqueous solution is lower than 40% by weight, though the aqueous solution may be handled stably, it will require the apparatus used for the storage or transportation thereof to be so enlarged as to render the work of storage or transportation uneconomical. Conversely, if this concentration exceeds 70% by weight, the aqueous solution will precipitate crystals so much as to render the handling thereof difficult. So long as the concentration of the aqueous solution is in the range mentioned above, the aqueous solution can be handled stably even when the iminocarboxylic acid salt is a sodium salt.

The third essential requirement for the method of handling according to this invention resides in adjusting the pH value of the aqueous iminocarboxylic acid salt solution in the range of 7 to 12. If the pH value of the aqueous iminocarboxylic acid salt solution is lower than 7, the aqueous solution will precipitate the salt of iminocarboxylic acid and will no longer be handled as a homogeneous aqueous solution. Conversely, if the pH value exceeds 12, the aqueous solution while in storage will undergo coloration and suffer decomposition of the iminocarboxylic acid salt to the extent of impairing the quality of the aqueous solution as a product. When the pH value of the aqueous iminocarboxylic acid salt solution is unduly high, it is lowered to a level in the range of 7 to 12 by the use of such an inorganic acid as hydrochloric acid, sulfuric acid, or phosphoric acid or such an organic acid as maleic acid, tartaric acid, or acetic acid. When this pH value is unduly low, it is heightened to a level in the same range by the use of an alkali metal hydroxide such as sodium hydroxide.

According to this invention, when the three essential requirements mentioned above are satisfied, the iminocarboxylic acid salt can be handled as a stable and homogeneous aqueous solution for a long time without suffering either precipitation of crystals or solidification of the aqueous solution. Moreover, the aqueous iminocarboxylic acid salt solution has viscosity not exceeding 10,000 cps and, therefore, can be easily handled.

The present invention imposes no particular limit on the temperature at which the aqueous iminocarboxylic acid salt solution is to be handled. The aqueous iminocarboxylic acid salt solution can be handled at any arbitrary temperature. The method of handling according to this invention manifests particularly conspicuously the action and effect thereof under such harsh temperature conditions as −10° to 70° C., especially at low temperatures in the range of −10° to 10° C. or at high temperatures in the range of 30° to 70° C. In a preferred embodiment of this invention, therefore, the aqueous iminocarboxylic acid salt solution is handled at temperatures in the range of −10° to 10° C. or in the range of 30° to 70° C. By the method of handling of this invention, the aqueous iminocarboxylic acid salt solution of such a high concentration as mentioned above is easily handled without suffering precipitation of crystals or solidification of the solution at low temperatures of less than 10° C. and without entraining decomposition or coloration of the iminocarboxylic acid salt during the course of protracted storage at high temperatures exceeding 30° C. If the temperature of handling is lower than −10° C., the flowability of the aqueous solution will be extremely lowered possibly to the extent of rendering the conveyance or transportation of the aqueous solution difficult. Conversely, if this temperature exceeds 70° C., the iminocarboxylic acid salt itself will decompose possibly to the extent of causing a decline of the purity of the product.

The aqueous iminocarboxylic acid salt solution is obtained by causing an aspartate to react with an epoxysuccinate or a maleate in a water medium as described above. There are times when the raw materials for the reaction will be so prepared that the reaction solution or the aqueous iminocarboxylic acid salt solution obtained after the completion of the reaction contains the iminocarboxylic acid salt at a concentration of less than 40% by weight for the purpose of preventing the possible precipitation of crystals during the course of the reaction. The aqueous iminocarboxylic acid salt solution obtained in this case must be concentrated by heating until the iminocarboxylic acid salt concentration reaches a level in the range of 40 to 70% by weight. This concentration by heating is properly carried out at a temperature in the range of 30° to 80° C. at a pH value in the range of 7 to 12. If this temperature exceeds 80° C., part of the iminocarboxylic acid salt will be decomposed and colored possibly to the extent of seriously impairing the value of the product. The concentration performed at a temperature lower than 30° C. is not appropriate from the commercial point of view because it requires the pressure to be markedly decreased. If the concentration is carried out at a pH value of lower than 7, the aqueous iminocarboxylic acid salt solution will adversely induce separation of the salt. Conversely, if it is carried out at a pH value exceeding 12, the disadvantage arises that the aqueous iminocarboxylic acid salt solution will be colored.

In one embodiment of this invention, therefore, the aqueous solution of an iminocarboxylic acid salt resulting from the reaction of an aspartate with an epoxysuccinate and containing an aspartic acid backbone moiety whose molar ratio of isomers, D form and L form, is in the range of 1/0 to 0.7/0.3 or 0/1 to 0.3/0.7 is concentrated by heating at a temperature in the range of 30 to 80° C. and a pH in the range of 7 to 12 to prepare an aqueous iminocarboxylic acid salt solution having a concentration in the range of 40 to 70% by weight and a pH value in the range of 7 to 12. The aqueous iminocarboxylic acid salt solution thus prepared is handled at a temperature in the range of 30° to 70° C. In this manner, the iminocarboxylic acid salt can be prevented from being colored during the course of the concentration of the aqueous solution thereof and, at the same time, can be handled in the form of a stable and homogeneous aqueous solution which suffers neither precipitation of the salt in the aqueous solution nor solidification of the aqueous solution.

The method of handling according to this invention allows an iminocarboxylic acid salt to be handled in the form of a constantly homogeneous aqueous solution. This aqueous solution, therefore, can be stored in a container for storage, conveyed as from a reaction vessel or a storage tank via a pipe directly to a site for actual use, or transported by means of a tank lorry, a tank car, a container, or a drum to a destination without requiring any special device such as for heat retention or agitation. The gaseous phase which is used in a vessel being used for storing or transporting the aqueous solution has no particular restriction. An inert gas such as nitrogen or argon or the air may be used as the gaseous phase.

When the aqueous iminocarboxylic acid salt solution is handled as when it is stored in a tank, for example, the material to be used for constructing the tank may be carbon steel, stainless steel, Hastelloy steel, titanium alloy steel, or nickel steel. The portion of the tank which is destined to contact the aqueous iminocarboxylic acid salt solution may be lined with glass, resin such as Teflon (tetrafluoroethylene), or rubber. Among other materials mentioned above, stainless steel is used particularly properly.

Now, this invention will be described more specifically below with reference to working examples.

Synthesis 1

In a four-necked flask provided with a stirrer and a reflux condenser, 88 g of disodium epoxysuccinate, 88.5 g of disodium L-aspartate, and 210 g of water were placed and left reacting at 80° C. for 8 hours. The reaction solution resulting from this reaction was analyzed by high-speed liquid chromatography with an instrument (produced by Shimadzu Seisakusho Ltd. and marketed under product code of "LC-10A"). As a result, it was found to contain 165 g of tetrasodium salt of iminocarboxylic acid having OH for R and Na for X or Y in the formulas (I) and (II) and an L form (D/L molar ratio=0/1).

Synthesis 2

An aqueous solution containing 164.5 g of tetrasodium iminocarboxylate having OH for R and Na for X or Y in the formulas (I) and (II) and a D form (D/L molar ratio=1/0) was obtained by following the procedure of Synthesis1 while using disodium D-aspartate in the place of disodium L-aspartate.

Synthesis 3

An aqueous solution containing 162.4 g of tetrasodium iminocarboxylate having OH for R and Na for X or Y in the formulas (I) and (II) and a L form (D/L molar ratio=0/1) was obtained by following the procedure of Synthesis 1 while using 334 g of an aqueous disodium L-aspartate solution (concentration 26.5% by weight) and 293 g of an aqueous disodium epoxysuccinate solution (concentration 30% by weight) instead.

EXAMPLES 1 TO 8 AND 10 to 15 AND CONTROLS 1 to 5

Aqueous tetrasodium iminocarboxylate solutions having such D form/L form molar ratios, pH values, and concentrations as are shown in Table 1 were prepared by mixing an aqueous tetrasodium L-iminocarboxylate solution and an aqueous tetrasodium D-imino-carboxylate solution obtained in Syntheses 1 and 2 at pertinent ratios. These aqueous solutions were put to storage at the temperatures shown in Table 1. The aqueous solutions immediately after their preparation were examined as to their appearance and that after one month's storage were similarly examined. The results are shown in Table 1. The aqueous solutions immediately after their preparation were tested for viscosity. The results are also shown in Table 1.

It is clearly noted from the results of Table 1 that the tetrasodium iminocarboxylates could be handled each in the form of a stable and homogeneous aqueous solution when the four essential requirements mentioned above were satisfied.

EXAMPLE 9

The aqueous tetrasodium L-iminocarboxylate solution having a concentration of 26% by weight and obtained in Synthesis 3 was concentrated by the use of a rotary evaporator at an inner temperature of 70° C. until the concentration rose to 55% by weight. During the course of this concentration, the aqueous solution was not found to assume any color. The aqueous solution resulting from the concentration was put to storage under the conditions shown in Table 1. The aqueous solution immediately after its preparation was examined as to its appearance and that after one month's storage was similarly examined. The results are shown in Table 1. The aqueous solution immediately after its preparation was tested for viscosity. The results are also shown in Table 1.

TABLE 1

|  | D/L (molar ratio) | pH | Concentration (% by weight) | Viscosity (cps) | Handling temperature (° C.) | Appearance of aq. soln. Immediately after preparation | After one month's storage |
|---|---|---|---|---|---|---|---|
| Example 1 | 0/1 | 11 | 50 | 200 | 30 | Colorless transparent | Colorless transparent |
| Example 2 | 0.3/0.7 | 11 | 50 | 200 | 30 | Colorless transparent | Colorless transparent |
| Example 3 | 0.7/0.3 | 11 | 50 | 200 | 30 | Colorless transparent | Colorless transparent |
| Example 4 | 1/0 | 11 | 50 | 200 | 30 | Colorless transparent | Colorless transparent |
| Example 5 | 0/1 | 11 | 60 | 9,000 | 30 | Colorless transparent | Colorless transparent |
| Example 6 | 0/1 | 9 | 50 | 250 | 30 | Colorless transparent | Colorless transparent |
| Example 7 | 0/1 | 8 | 50 | 250 | 30 | Colorless transparent | Colorless transparent |
| Example 8 | 0/1 | 11 | 60 | 2,000 | 50 | Colorless transparent | Colorless transparent |
| Example 9 | 0/1 | 11 | 55 | 450 | 40 | Colorless transparent | Colorless transparent |
| Example 10 | 0/1 | 11 | 50 | 7,000 | 0 | Colorless transparent | Colorless transparent |
| Example 11 | 0.3/0.7 | 11 | 50 | 7,000 | 0 | Colorless transparent | Colorless transparent |
| Example 12 | 0.7/0.3 | 11 | 50 | 7,000 | 0 | Colorless transparent | Colorless transparent |
| Example 13 | 1/0 | 11 | 50 | 7,000 | 0 | Colorless transparent | Colorless transparent |
| Example 14 | 0/1 | 11 | 40 | 200 | −10 | Colorless transparent | Colorless transparent |
| Example 15 | 0/1 | 11 | 50 | 2,200 | 10 | Colorless transparent | Colorless transparent |
| Control 1 | 0.5/0.5 | 11 | 50 | 200 | 30 | Colorless transparent | White slurry |
| Control 2 | 0.4/0.6 | 11 | 50 | 200 | 30 | Colorless transparent | White slurry |
| Control 3 | 0.6/0.4 | 6 | 50 | 230 | 30 | Colorless transparent | White slurry |
| Control 4 | 0.6/0.4 | 13 | 50 | 30 | 70 | Colorless transparent | Yellow slurry |
| Control 5 | 0.5/0.5 | 11 | 60 | 85,000 | 20 | Colorless transparent | White solid |

What is claimed is:

1. A method for handling an iminocarboxylic acid salt represented by the formula (I):

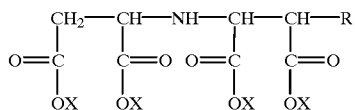

(I)

wherein R is a hydrogen atom or a hydroxyl group and X is a sodium atom or an ammonium group, which comprises:
handling the salt in the form of an aqueous solution wherein the salt contains an aspartic acid backbone moiety whose molar ratio of the isomers, designated as D form/L form is in the range of 1/10 to 0.7/0.3, or D form/L form in the range of 0/1 to 0.3/0.7, and accounts for a concentration in the range of 40 to 70% by weight, said method of handling selected from the group consisting of transporting the aqueous solution by means of a tank lorry, storing thereof as in a tank, and conveying thereof as by piping including pipes, valves and nozzles.

2. A method according to claim 1, wherein the concentration of said aqueous solution is in the range of 40 to 60% by weight.

3. A method according to claim 1, wherein the molar ratio of D form/L form is in the range of 0/1 to 0.3/0.7.

4. A method according to claim 1, wherein X in the formula (I) is a sodium atom.

5. A method according to claim 1, wherein the aqueous solution has a pH in the range of 7 to 12.

6. A method according to claim 1, wherein the temperature of the aqueous solution is in the range of −10 to +70° C.

7. A method according to claim 6, wherein the temperature of the aqueous solution is in the range of −10 to +10° C. or 30 to 70° C.

8. A method according to claim 1, wherein the salt in the form of an aqueous solution is prepared by causing an aspartate to react with an epoxysuccinate or a maleate in an aqueous medium.

* * * * *